(12) United States Patent
Hu

(10) Patent No.: US 10,329,240 B2
(45) Date of Patent: Jun. 25, 2019

(54) PROCESS FOR THE SEPARATION OF LONG CHAIN AMINO ACIDS AND DIBASIC ACIDS

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/644,665

(22) Filed: Jul. 7, 2017

(65) Prior Publication Data

US 2019/0002396 A1    Jan. 3, 2019

Related U.S. Application Data

(63) Continuation-in-part of application No. 15/635,874, filed on Jun. 28, 2017, now Pat. No. 9,969,676.

(51) Int. Cl.
  *C07C 227/42*   (2006.01)
  *C07C 227/40*   (2006.01)
  (Continued)

(52) U.S. Cl.
  CPC .............. *C07C 227/42* (2013.01); *B01D 3/36* (2013.01); *B01D 9/0004* (2013.01);
  (Continued)

(58) Field of Classification Search
  CPC ..... C07C 51/48; C07C 259/06; C07C 275/42; C07C 311/21; C07C 317/44; C07C 45/46;
  (Continued)

(56) References Cited

U.S. PATENT DOCUMENTS 2,700,054 A * 1/1955 White .................. C07C 227/08
                                                562/559
2,776,990 A    1/1957 Hines
(Continued)

FOREIGN PATENT DOCUMENTS

SU    1209680 A1 *  2/1986
SU    1209680 A1    2/1986
(Continued)

OTHER PUBLICATIONS

Bowen C.V. "Distribution of Anabasine between Certain Organic Solvents and Water." Industrial & Engineering Chemistry, vol. 41, 1949, p. 1295-1296. (Year: 1949).*
(Continued)

*Primary Examiner* — Deborah D Carr
(74) *Attorney, Agent, or Firm* — Myers Wolin, LLC

(57) ABSTRACT

There is disclosed a process for the separation of long chain amino acid and long chain dibasic acid, comprising: (1) recovering alkylamine from an aqueous solution of an alkali hydroxide hydrolysis of the mixed amide derivatives by distilling or by extracting with an extractant solvent; (2) cooling the aqueous solution of step (1) to precipitate a mixed alkali salts of long chain amino acid and dibasic acid; (3) recovering the mixed alkali salts of long chain amino acid and dibasic acid to provide a mother liquor; (4) separating long chain amino acid and dibasic acid by acidification-extraction of long chain dibasic acid with an extractant solvent or by selective dissolution of alkali salt of long chain amino acid in an aqueous solvent; and (4) adding an acid to the mother liquor of step (3) to obtain alkanoic acid.

25 Claims, 12 Drawing Sheets

(51) Int. Cl.

| | |
|---|---|
| *C07C 51/44* | (2006.01) |
| *C07C 51/43* | (2006.01) |
| *C07C 209/86* | (2006.01) |
| *B01D 3/36* | (2006.01) |
| *B01D 9/00* | (2006.01) |
| *B01D 11/04* | (2006.01) |
| *C07C 51/46* | (2006.01) |
| *C07C 51/47* | (2006.01) |
| *C07C 51/48* | (2006.01) |
| *B01D 21/26* | (2006.01) |

(52) U.S. Cl.
CPC ......... *B01D 9/0018* (2013.01); *B01D 9/0059* (2013.01); *B01D 11/0488* (2013.01); *B01D 11/0492* (2013.01); *C07C 51/43* (2013.01); *C07C 51/44* (2013.01); *C07C 51/46* (2013.01); *C07C 51/47* (2013.01); *C07C 51/48* (2013.01); *C07C 209/86* (2013.01); *C07C 227/40* (2013.01); *B01D 21/262* (2013.01)

(58) Field of Classification Search
CPC ..... C07C 49/697; C07C 53/126; C07C 55/02; C07C 55/20; C07C 55/21; C07C 59/64; C07C 205/56; C07C 227/18; C07C 259/10; C07C 311/13; C07C 311/29; C07C 311/44; C07C 323/56; C07C 51/06; C07C 209/365; C07C 209/86; C07C 227/40; C07C 227/42; C07C 229/46; C07C 233/18; C07C 317/00; C07C 49/255; C07C 51/43; C07C 51/44; C07C 51/46; C07C 51/47; C07C 57/58; C07C 57/60; C07C 57/62; C07C 59/72; C07C 59/74; C07C 59/88; C07C 69/42; C07C 69/716; C07C 233/09; C07C 237/14; C07C 243/00; C07C 255/31; C07C 2601/08; B01D 11/0492; B01D 3/36; B01D 9/0004; B01D 9/0018

USPC .................. 554/114, 191, 192, 211, 212
See application file for complete search history.

(56) References Cited

U.S. PATENT DOCUMENTS

| | | | |
|---|---|---|---|
| 2,960,533 A | | 11/1960 | Frank et al. |
| 2,998,357 A | | 8/1961 | Gilette et al. |
| 3,541,121 A | | 11/1970 | Crandall et al. |
| 4,496,736 A | * | 1/1985 | Bonse ............ C07C 51/06 546/319 |
| 5,770,765 A | * | 6/1998 | Ohkoshi ............ C07C 51/265 562/414 |
| 2004/0082042 A1 | | 4/2004 | Staley |

FOREIGN PATENT DOCUMENTS

| | | | | |
|---|---|---|---|---|
| WO | 2017088218 A1 | | 6/2017 | |
| WO | WO-2017088218 | * | 6/2017 | ......... C07C 227/18 |

OTHER PUBLICATIONS

International Search Report with the International Search Opinion issued for corresponding International Patent Application No. PCT/US2018/039132 dated Sep. 27, 2018.

Bowen C.V. "Distribution of Anabasine between Certain Organic Solvents and Water." Industrial & Engineering Chemistry, vol. 46, No. 6, 1949, p. 1295-1296, Table 1.

International Search Report with the International Search Opinion issued for corresponding International Patent Application No. PCT/US2018/039135 dated Sep. 27, 2018.

International Search Report and Written Opinion issued for International Patent Application No. PCT/US2018/039139 dated Oct. 18, 2018.

Bowen C.V. "Distribution of Anabasine between Certain Organic Solvents and Water." Industrial & Engineering Chemistry, vol. 41, 1949, p. 1295-1296.

International Search Report with the International Search Opinion issued for corresponding International Patent Application No. PCT/US2018/039128 dated Oct. 4, 2018.

\* cited by examiner

PROCESS FOR THE SEPARATION OF LONG CHAIN AMINO ACIDS AND DIBASIC ACIDS

CROSS REFERENCE

This application is a continuation-in-part of the co-pending application Ser. No. 15/635,874, filed on Jun. 28, 2017, which is incorporated herein by reference.

TECHNICAL FIELD

The present invention relates to a process for the separation of long chain amino acids, long chain dibasic acids, short chain alkylamines, and short chain alkanoic acids.

BACKGROUNDS OF THE INVENTION

Long chain saturated aliphatic amino acids, lactams, and dibasic acids are important monomers for long chain nylons and engineering plastics. Nylons are a class of polymers that contain amide bond on their backbone of chains. Nylons are one of the most widely used, most numerous in types, and most consumed class of engineering plastics.

Because of their unusual molecular structure, long chain nylons possess extraordinary physical properties, i.e., higher mechanical strength than metal, low hygroscopicity, excellent resistance to oil, low temperature, abrasion, and chemical corrosion, and most importantly, easy to fabricate. Long chain nylons are made into many kinds of plastics products, spun to fibers, and stretched to thin films. Long chain nylons are also used in paints and hot melt adhesives. Hence, long chain nylons find wide applications in automobile, electrical, electronic, telecommunications, petrochemical, and aerospace industries.

Long chain amino acids and lactams are used industrially as monomers to produce nylon-9, nylon-11, and nylon-12.

Long chain dibasic acids are condensed with diamines industrially as starting materials to produce nylon-610, nylon-612, nylon-510, nylon-512, nylon-1010, and nylon-1212.

WO 2017/088218 and the co-pending U.S. Ser. No. 15/601,556 both by the present inventor, both of which are incorporated by reference herein, disclose a novel process for the coproduction of long chain amino acids and dibasic acids from keto fatty acid derivatives. According to the disclosed process, long chain keto fatty acid derivatives are reacted with hydroxylamine to form an oxime derivative, which is subjected to the Beckmann rearrangement to yield a mixture of two amide derivatives. These amide derivatives are hydrolyzed to a mixture of products containing long chain amino acids and dibasic acids, which are isolated by a process of step-wise neutralization in a highly dilute concentration. Thus, a substantial amount of energy is required for the concentration, so that the process is not economical.

Moreover, the present inventor has found that long chain amino acids and dibasic acids of required quality for the production of polyamides cannot be obtained, if the process according these prior disclosures is applied for commercial starting materials, which contain various amount of other fatty acids. Apparently, these impurities contaminate intended products and thus demand a process for their removal from final products of required purity.

Hydrolysis of the mixed amide derivatives from the Beckmann rearrangement yields not only long chain amino acids and dibasic acids, but also short chain alkyl amines and alkanoic acids. There is a lack of any method for the separation and recovery of these short chain products from the mixture of the hydrolysis reaction.

It is desirable to have a process for the separation of each component to their required purity from their complex mixture to achieve an economical process and to reduce or eliminate the disposal of waste stream.

It is an object of the present invention to disclose a process for the separation of long chain amino acids, dibasic acids, short chain alkyl amines, short chain alkanoic acids, and for the recovery of other fatty acids present in the commercial starting materials, such as stearic acid, and impurities generated as byproducts of the production reactions. By the process of the present invention, long chain amino acids and dibasic acids are separated simply, efficiently, and economically with high yields and excellent purity.

It is another object of the present invention to disclose a process for the recovery of long chain amino acids and inorganic salts from aqueous waste mother liquor. As a result, there is no aqueous waste discharge from production process.

DESCRIPTION OF THE INVENTION

Hydrolysis of the mixed amide derivatives of the following structures:

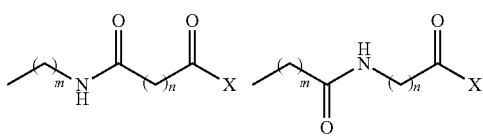

from the Beckmann rearrangement of oxime fatty acid derivatives can be carried out with either an acid or a base to yield a mixture of main products of the following structures:

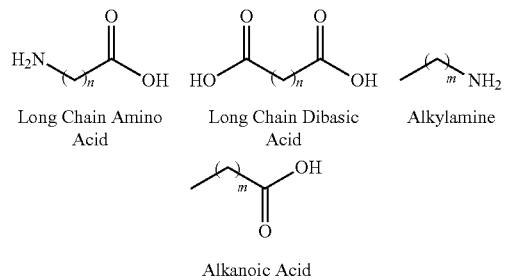

Long Chain Amino Acid     Long Chain Dibasic Acid     Alkylamine

Alkanoic Acid wherein m is an integral from 0 to 10, n is an integral from 6 to 20; X is OR or $NR_1R_2$, wherein OR is OH, $C_1$-$C_8$ monohydric alcohol or $C_1$-$C_8$ polyhydric alcohol, and $R_1$ and $R_2$ are each independently hydrogen or $C_1$-$C_8$ alkyl group.

When m=5, n=10, the main products are 11-aminoundecanoic acid, dodecanedioic acid, hexylamine, and heptanoic acid. Because the starting material of commercial grade is obtained from castor oil, significant amount of stearic acid is also present as an impurity in the mixture of products.

When m=7, n=8, the main products are 9-aminononanoic acid, sebacic acid, octylamine, and pelargonic acid.

When m=5, n=12, the main products are 13-aminotridecanoic acid, tetradecanedioic acid (brassylic acid), hexylamine, and heptanoic acid.

Figure 6:
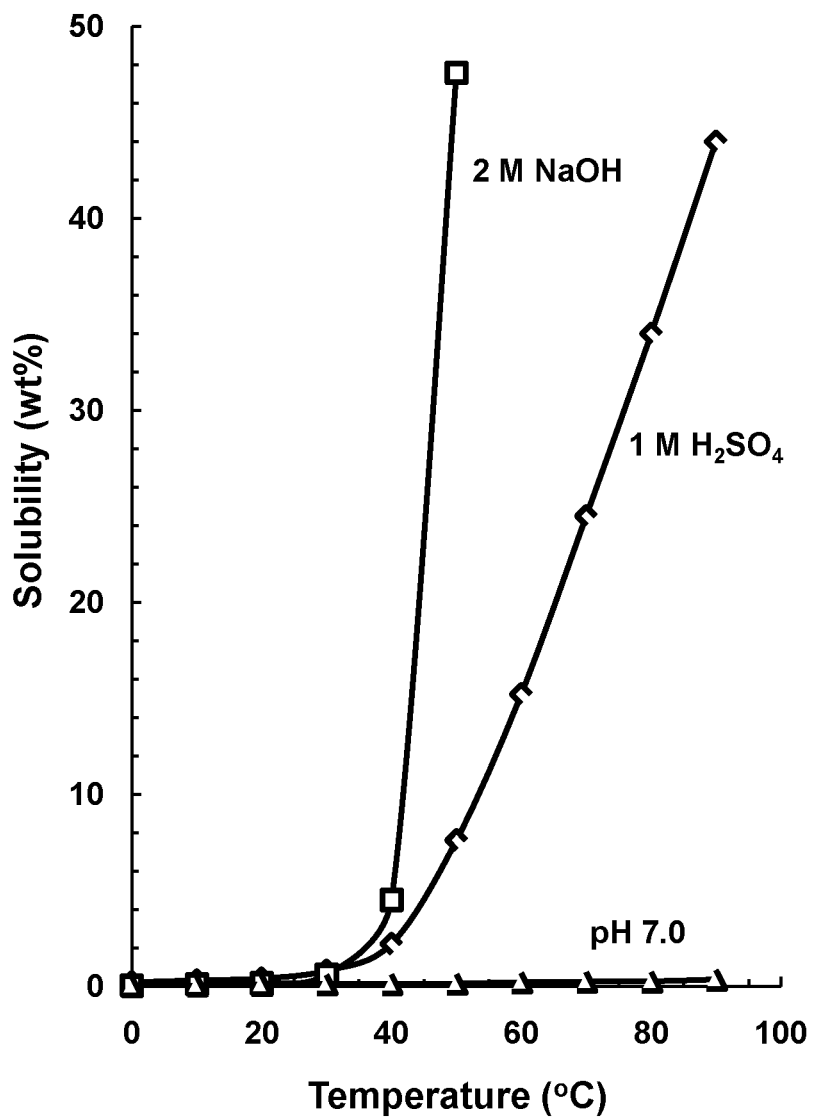
FIG. 6. Solubility curve of 11-aminoundecanoic acid in water at neutral pH, 1 M solution of sulfuric acid, and 2 M solution of sodium hydroxide.

When the hydrolysis reaction of mixed amide derivatives from the Beckmann rearrangement is performed in the presence of alkali hydroxide, main products other than alkylamine are obtained in the form of their alkali salts. It was observed that a starting suspension of the mixed amide derivatives in a solution of alkali hydroxide is changed to a clear solution at a temperature of 60° C. or above after the hydrolysis. Upon cooling, the clear solution becomes a pasty, non-stirrable cake, because alkali salts of long chain amino acids and dibasic acids are nearly insoluble in an alkali solution as shown in FIG. 6.

The alkali metals are lithium, sodium, potassium, or cesium.

Figure 1:
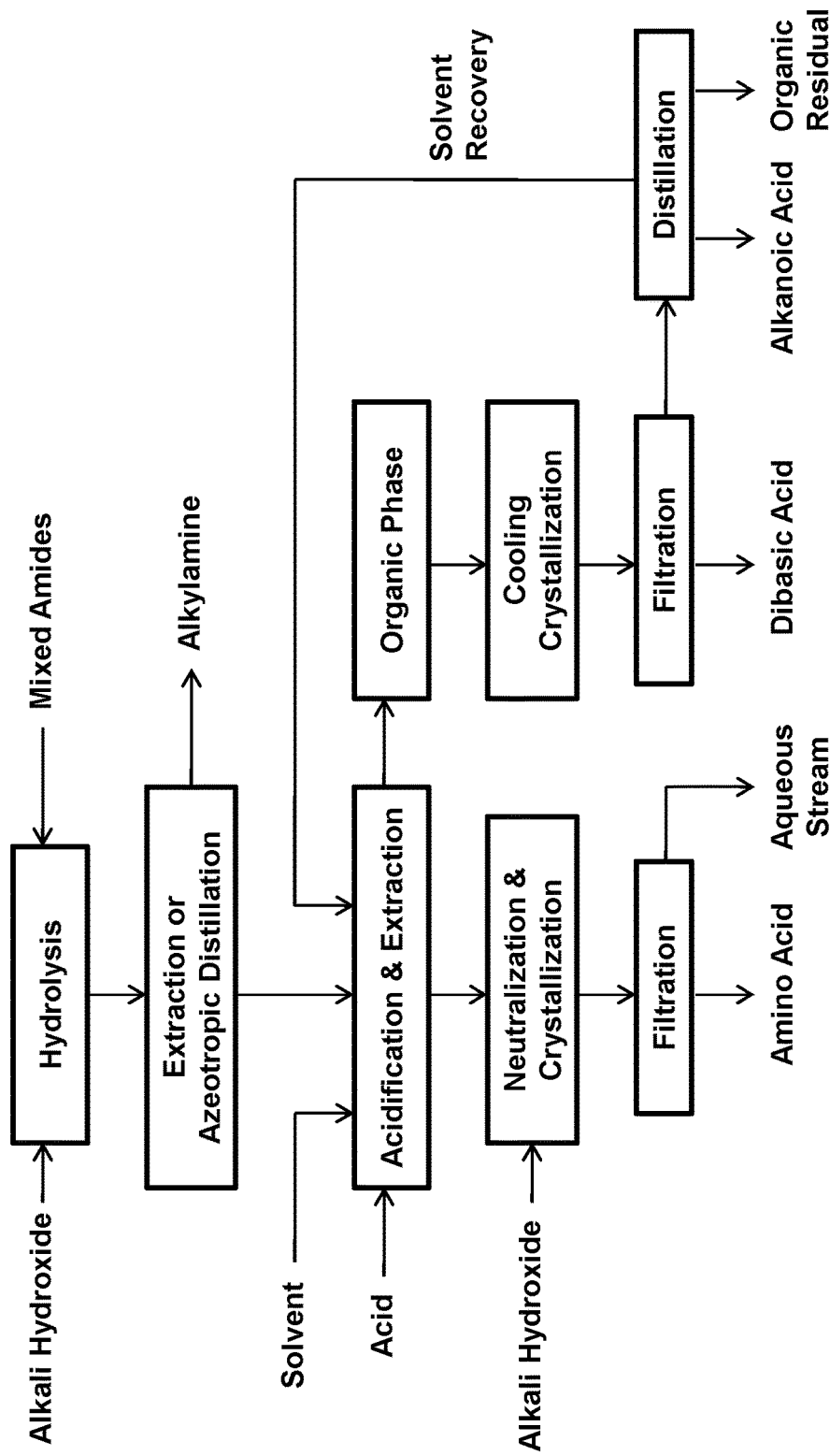
FIG. 1. Schematic flowchart for the separation of long chain amino acid, dibasic acid, alkylamine, and alkanoic acid from their mixture in the case of an alkali hydroxide hydrolysis.
Figure 2:
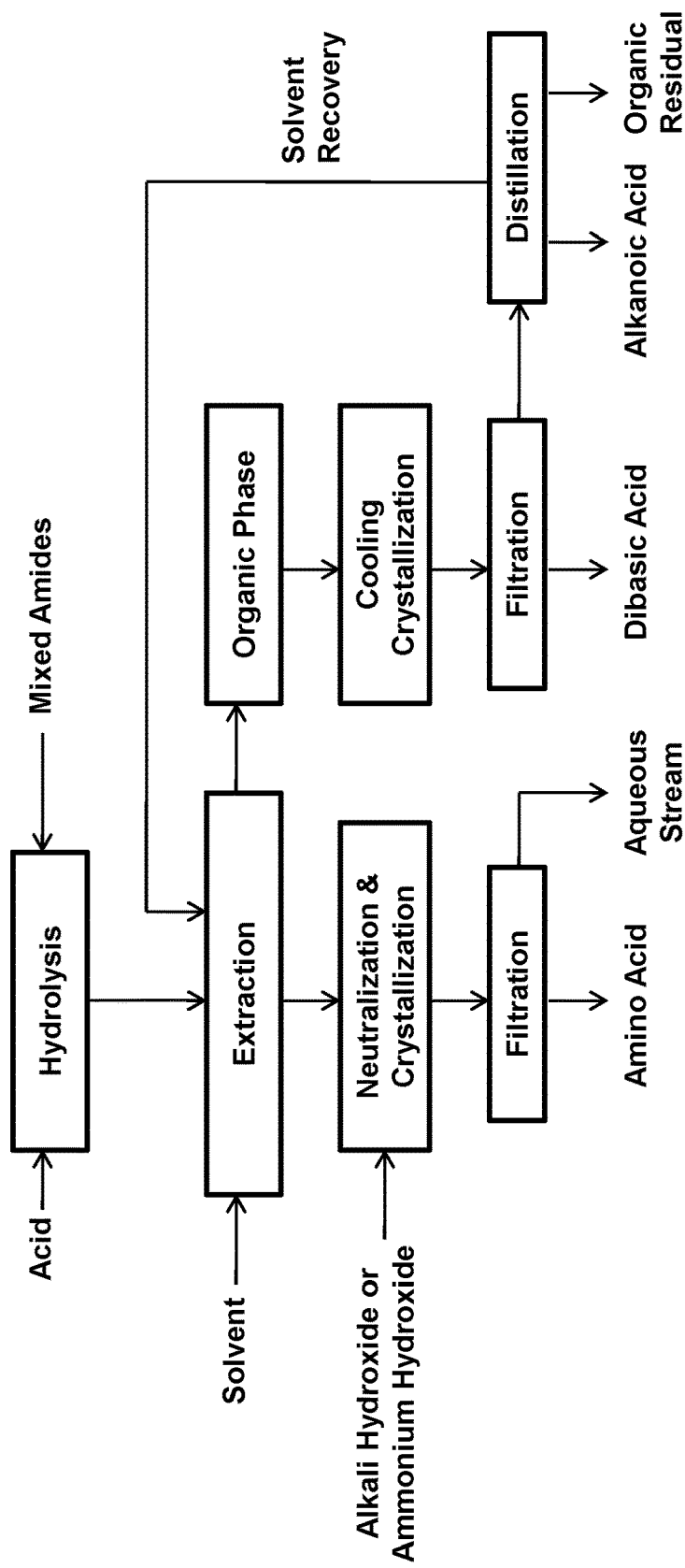
FIG. 2. Schematic flowchart for the separation of long chain amino acid, dibasic acid, alkylamine, and alkanoic acid from their mixture in the case of an acid hydrolysis.

The process according to the present invention, illustrated in FIG. 1 for the separation of each component in a mixture of the hydrolysis reaction by the method of alkali hydroxide, starts with removal of low-boiling components and alkylamine.

The low boiling component comes from alcohols, i.e., methanol or ethanol, commonly used in the starting material of keto fatty acid esters. If the mixed amide derivatives are carboxylic acid, little or no low boiling component is present in the mixture.

These low boiling alcohols, formed by the hydrolysis of esters, are distilled off from the reaction mixture. Distillation of these low boiling alcohols can be carried out under normal pressure, increased pressure, or reduced pressure, during or after the hydrolysis reaction.

Some alkylamines, in particular, of $C_1$ to $C_5$, are of lower boiling point, and they are distilled off along with alcohols. These alkylamines can be separated from alcohols according to methods known in prior art.

For the production of 11-aminoundecanoic acid and dodecanedioic acid, hexylamine is one of the main products. Hexylamine is found to form an azeotrope with water and can be separated from the solution by azeotropic distillation. Upon cooling, the distillate separates into an upper phase of nearly pure hexylamine and an aqueous phase containing not more than 2% of hexylamine. Hexylamine can also be separated from the mixture by steam distillation or steam stripping. Complete separation is accomplished when the distillate at the overhead becomes nearly neutral at a pH of 7-8.

The hexylamine distillate contains a small percentage of water and can be dried with a drying agent, and preferably, by azeotropic distillation of a small amount of hexylamine to remove the water in hexylamine.

Hexylamine and alkylamines of more than $C_7$ can also be separated from the hydrolysis solution by extraction with an extractant solvent. These alkylamines show excellent partition properties between an organic extractant phase and the strongly alkaline aqueous mixture of the hydrolysis reaction. Suitable extractant solvents are selected from the classes of ester, aliphatics, aromatics, ethers, ketones, and water-insoluble amines. Preferably, selected extractant solvent is the same as the solvent chosen for the next stage of the process according to the present invention.

Long chain amino acids and dibasic acids exhibit similarly low solubility through a wide range of pH from 2 to 10 at room temperature. Their separation from each other necessitates a high dilution with great difficulty even when their mixture is not contaminated by other impurities of similar properties, such as fatty acids. When the commercial starting materials, which invariably contain many other fatty acids, are used in the process according to previous disclosure, the products, long chain amino acids and dibasic acids, are always contaminated with these fatty acids.

The present inventor carried out extensive studies to overcome the inherent problems imposed by their little difference in solubility for long chain amino acids and dibasic acids and found in the present invention that the solubility of long chain amino acids can be greatly increased by reacting these amino acids with an acid to form an acid salt at increased temperature. At the same time, alkali salts of long chain dibasic acids and fatty acids in the solution are turned into their free carboxylic acids, which can be dissolved in an organic solvent. Complete separation of these long chain amino acids from long chain dibasic acids and fatty acids is thus accomplished by forming an aqueous solution of an acidic salt of these long chain amino acids and an organic extractant phase rich in long chain dibasic acids, short chain alkanoic acids, and fatty acids.

Suitable acids are an acid of a pKa<5.0. These acids are, but not limited to, inorganic acids, i.e., hydrochloric acid, hydrobromic acid, hydroiodic acid, sulfuric acid, nitric acid, phosphoric acid; alkyl and aryl sulfonic acids, i.e., methanesulfonic acid, ethanesulfonic acid, propanesulfonic acid, isethionic acid, benzenesulfonic acid, toluenesulfonic acid, xylenesulfonic acid, and sulfamic acid; organic carboxylic acids: malic acid, maleic acid, tartaric acid, glycolic acid, lactic acid, citric acid, oxalic acid, formic acid, acetic acid, and propionic acid. One or a mixture of two or more of these acids can be used to form an acidic salt of long chain amino acids.

Preferably, the acid is selected from one of the inorganic acids, and most preferably, sulfuric acid.

The aim of acidification is to completely convert alkali salts of long chain dibasic acids, short chain alkanoic acids, and fatty acids into free carboxylic acids and to form an acid salt of long chain amino acid, so as to ensure complete dissolution of long chain amino acid in aqueous phase and long chain dibasic acid in an organic extractant phase.

Organic solvents suitable for extracting dibasic acids and fatty acids are water-insoluble and belong to the classes of ester, aliphatics, aromatics, ethers, alcohols of $C_4$ to $C_{10}$ and ketones of $C_4$ to $C_{10}$. Useful solvents include, but not limited to, butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone. A single solvent or a mixture of two or more solvents can be used as extractant solvent.

Selected extractant solvent is expected to have good solubility of long chain dibasic acid and fatty acid at higher temperature, low or little solubility at lower temperature for the long chain dibasic acid and good solubility for fatty acid or the like at lower temperature to ensure an effective separation of long chain dibasic acid from other fatty acids rich in the organic phase.

Preferably, the extractant solvent is toluene.

The amount of extractant solvent is not limited, but is greater than the effective amount for the dissolution of dibasic acids and fatty acid impurities.

Temperature to perform acidification and extraction is in the range from 50° C. to the boiling point of the mixture of extractant organic phase rich in long chain dibasic acid and fatty acid and below 100° C. under normal pressure. Acidification and extraction can also be carried out at elevated temperature under pressure, but pressure equipment will be needed for the process.

Preferably, acidification and extraction are performed at a temperature from 60° C. to 95° C., and most preferably at a temperature from 80° C. to 90° C. At higher temperature, the higher solubility of long chain dibasic acid in the extractant solvent is advantageous in reducing the amount of the extractant solvent used.

There is no preference as to how an acid and an extractant solvent are introduced into the solution of alkali salts of long chain amino acid and dibasic acid that have been freed of alkylamine. An acid and an extractant solvent can be added concomitantly, sequentially, continuously, semi-continuously, or batch wise.

When the acidification and extraction are performed according to the process of the present invention, good phase separation is achieved. The present inventor unexpectedly found that extractant solvent extracts nearly all colored materials into extractant phase, leaving behind a colorless aqueous solution of the acid salt of long chain amino acid, which provides an added advantage in greatly simplifying the purification of long chain amino acids.

The present inventor found that a middle phase between the upper extractant phase and lower aqueous phase is formed in some cases and contains predominantly the acid salt of long chain amino acid and the acid salt of hexylamine, if hexylamine is not removed or removed incompletely from the hydrolysis solution. This middle phase is formed, especially, when the aqueous solution contains a high concentration of alkali salt. However, the middle phase can be effectively separated and combined with aqueous phase to recover long chain amino acid. Alternatively, after separating the aqueous phase, the middle phase is dissolved with deionized water at increased temperature.

Although the aqueous solution of the acid salt of long chain amino acid is nearly colorless, to further improve the quality of the isolated product, the solution can be treated with activated carbon to decolorize and to absorb minor impurities. The treatment can be carried out from 50° C. to the boiling point for a period from a few minutes to a few hours, preferably 30 minutes to 2 hours, most preferably for 1 hour. After filtration, a clear colorless solution is obtained.

In order to isolate long chain amino acid, the strongly acidic aqueous solution is neutralized with a basic agent to near neutral acidity in a pH range from 5 to 9. More preferably, the pH is in the range of 6 to 8. The neutralization is performed at a temperature from 50° C. to the boiling point of the solution, preferably from 60 to 90° C., most preferably from 70° C. to 80° C. Neutralization at this most preferred temperature produces larger crystals that will facilitate solid-liquid separation. After cooling to 30° C. to 40° C., the product, long chain amino acid, is precipitated and separated by means of solid-liquid separation, i.e., filtration or centrifuge, to yield a mother liquor containing inorganic salt and a small amount of long chain amino acid.

The basic agent is selected from the group consisting of ammonia, alkali and ammonium salts of hydroxide, bicarbonate, carbonate, sulfite, bisulfite, and carboxylate. A single agent or a mixture of two or more agents can be used. Preferably, the basic agent is an alkali hydroxide, and most preferably, the same agent used in the hydrolysis reaction of the mixed amide derivatives.

The most preferable basic agent is sodium hydroxide.

Figure 3:
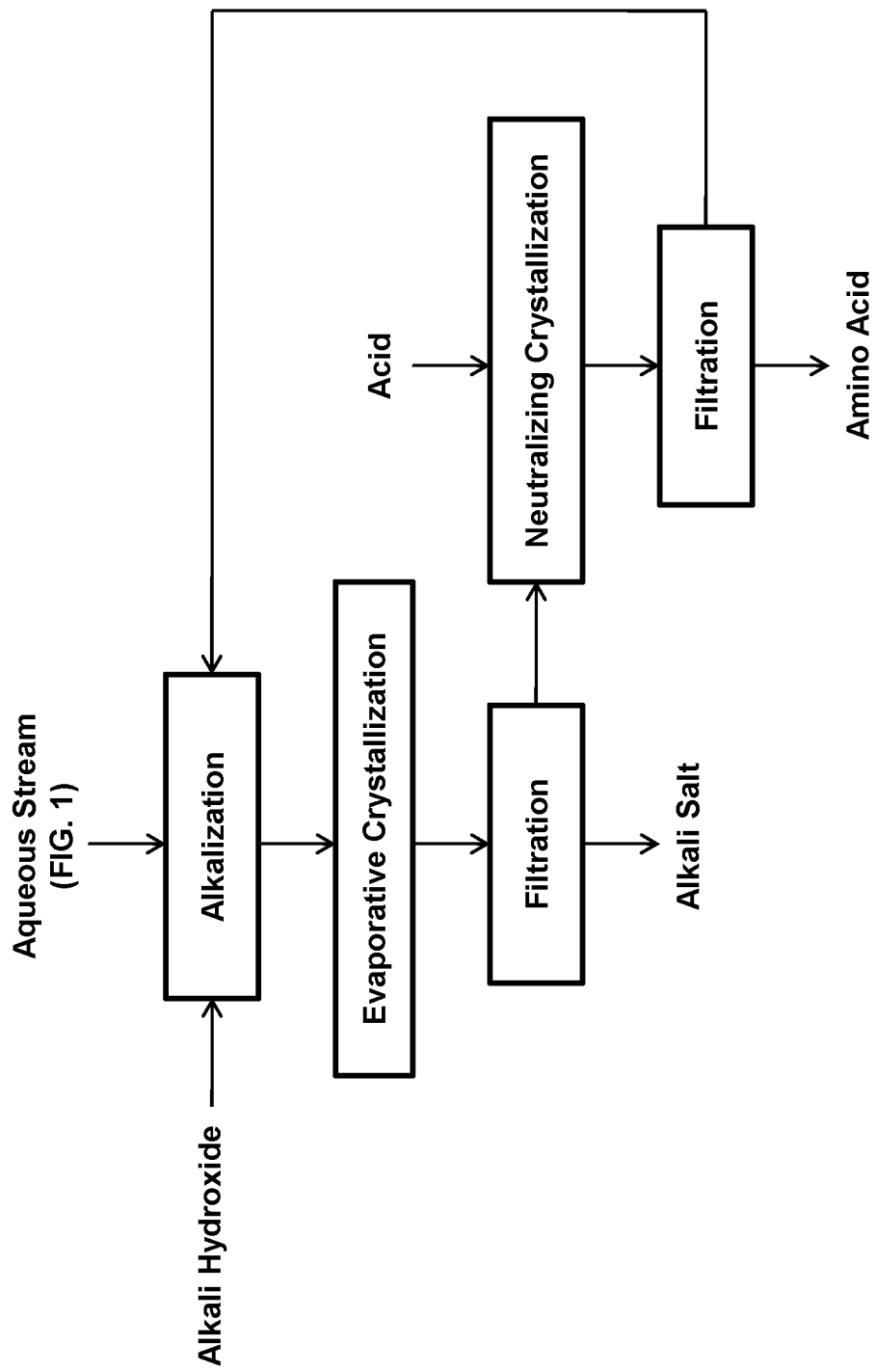
FIG. 3. Schematic flowchart for the recovery of long chain amino acid and alkali salt from waste aqueous stream with the aid of an alkali hydroxide.
Figure 4:
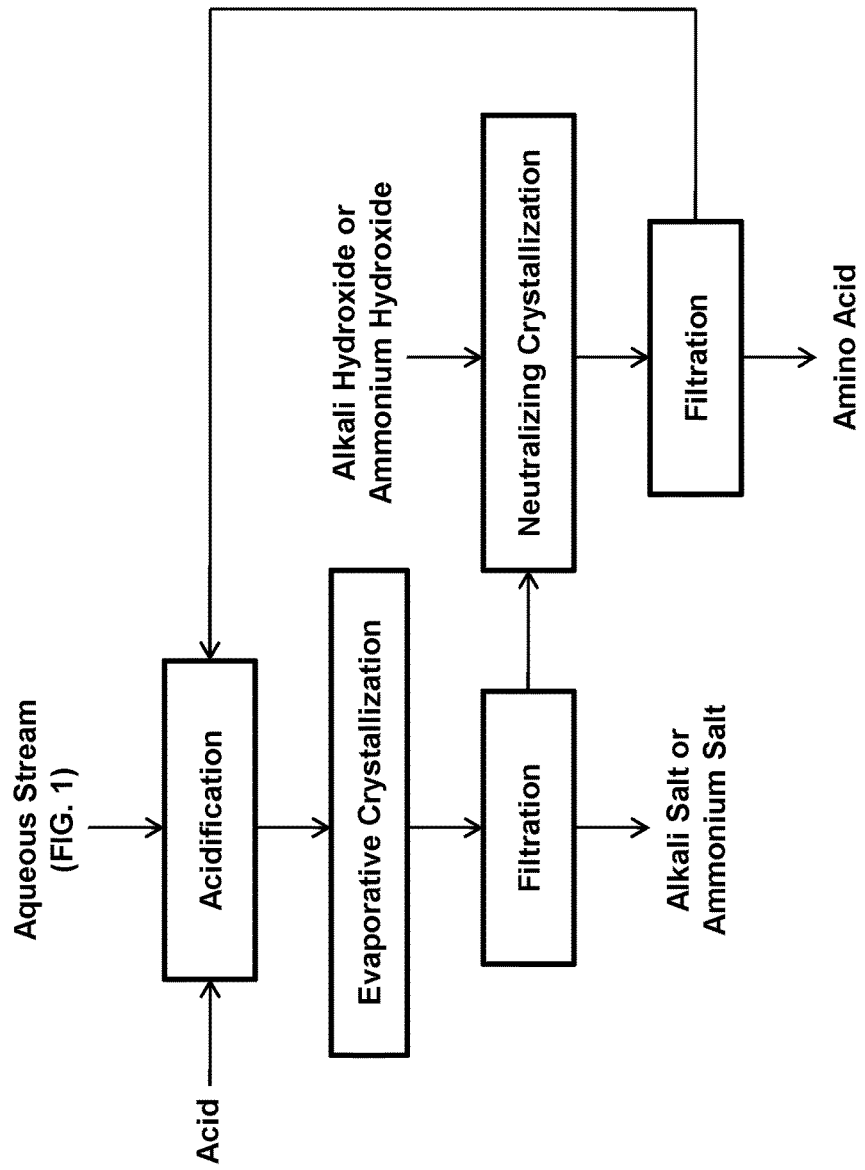
FIG. 4. Schematic flowchart for the recovery of long chain amino acid and alkali salt from waste aqueous stream with the aid of an acid.

Treatment of the mother liquor after the isolation of long chain amino acid is illustrated in FIG. 3 and FIG. 4 to achieve a complete separation of inorganic salt and full recovery of long chain amino acid with the aid of an alkali hydroxide or an acid, respectively.

Since long chain amino acid, e.g., 11-aminoundecanoic acid, has relatively constant solubility, evaporative concentration of the mother liquor will result in the crystallization of inorganic salt, in particular, sodium sulfate, along with valuable long chain amino acid. To overcome this difficulty, the present inventor found that the solubility of 11-aminoundecanoic acid can be drastically increased by increasing or lowering the pH at increased temperature as illustrated in FIG. 6. In fact, alkali salt of 11-aminoundecanoic acid becomes freely soluble in 2 M solution of sodium hydroxide at about 50° C. This finding greatly facilitates the separation of inorganic salt, most preferably, sodium sulfate, and the recovery of long chain amino acids.

Although the solubility of long chain amino acid can be increased by both an acid and an alkali hydroxide, it is preferable to use an alkali hydroxide, because alkali salt is non-corrosive to commonly used process equipments made of stainless steel.

After adjusting pH of the aqueous stream with an alkali hydroxide, the mother liquor is concentrated to crystallize inorganic salt, most preferably, sodium sulfate, at a temperature from 40° C. to the boiling point of the solution. Evaporative crystallization can be carried out under normal, reduced, or increased pressure, continuously or in batch. The crystallized salt is removed from the saturated solution by means of solid-liquid separation, e.g., filtration or centrifuge.

The basic mother liquor after removal of alkali salt is neutralized with an acid to a neutral pH. The dissolved long chain amino acid precipitates and can be recovered by means of solid-liquid separation, and the mother liquor is recycled.

The acid used in this step can be selected from the class of inorganic acids, organic carboxylic acids, organic sulfonic acids, sulfamic acid. Preferably, one of the inorganic acids is selected. More preferably, the same acid is used as in previous step. Most preferably, the acid is sulfuric acid.

The extractant phase rich in long chain dibasic acid, short chain alkanoic acid, and fatty acid after the separation of aqueous phase is cooled to a lower temperature in the range of 0° C. to 50° C., more preferably 0° C. to 30° C., most preferably 10° C. to 20° C. to crystallize long chain dibasic acid, which can be separated by means of solid-liquid separation. Although the extractant phase and filtration mother liquor is dark in color, the product is nearly white in color and free of any other fatty acids, such as stearic acid.

The mother liquor is distilled to recover extractant solvent and the residual is distilled under vacuum to recover short chain alkanoic acid, e.g., heptanoic acid, in nearly pure form.

In one embodiment of the present invention, the extractant phase is first concentrated by distillation, then cooled to crystallize long chain dibasic acid in an increased yield.

In another embodiment of the present invention, the extractant phase is first distilled to recover extractant solvent, then distilled under vacuum to recover short chain alkanoic acid. To the distillation residual is added an organic solvent to dissolve the residual by heating, then to crystallize long chain dibasic acid by cooling. The solvent is most preferably the original extractant solvent, so that no mixture of different solvents will result to simplify the overall process.

In a further embodiment of the present invention, the extractant phase is distilled to recover solvent and the residual is added to a lower alcohol, in particular methanol or ethanol, most preferably, methanol, in the presence of an esterification catalyst to yield a mixture of methyl esters of alkanoic acid, long chain dibasic acid, and other fatty acid originating from starting materials. These methyl esters are then fractionally distilled to obtain each component in pure form and are freed of any colored materials. These pure methyl esters are marketed directly or can be hydrolyzed to their respective carboxylic acid according to process known in prior art.

Alternatively, the mixture of methyl esters is distilled to a mixture that is freed of any colored materials. The distilled mixture of methyl esters are then hydrolyzed to a mixture of alkanoic acid, long chain dibasic acid, and fatty acid, which can be separated according to the process of the present invention.

In the case of producing 11-aminoundecanoic acid and dodecanedioic acid according to the process of the present invention, the distillation residual is black in color and contains stearic acid from the starting material of castor oil and a small amount of dodecanedioic acid. This dark residual is reacted with a lower alcohol, most preferably, methanol, in the presence of an acid catalyst to form methyl esters. The mixed methyl esters are fractionally distilled to yield colorless methyl esters of stearic acid and dodecanedioic acid. The recovered methyl stearate is either hydrolyzed to stearic acid or marketed as a commercial product, while the methyl ester of dodecanedioic acid is hydrolyzed to obtain dodecanedioic acid.

When the hydrolysis reaction of mixed amide derivatives from the Beckmann rearrangement is performed with an acid, most preferably, sulfuric acid, alkyl amine and long chain amino acid are obtained in the form of their acid salts, while long chain dibasic acid and fatty acid exist in the form of free carboxylic acid.

After the hydrolysis reaction proceeds to completion, water and an extractant solvent are introduced into the suspension to dissolve the acid salts of long amino acid and alkylamine and to transfer the long chain dibasic acid, short chain alkanoic acid, and other fatty acid into an extractant phase.

There is no preference as to how water and extractant solvent are added to the hydrolysis mixture. They can be added concomitantly, sequentially, continuously, semi-continuously, or batch wise. The amount of water added to the reaction mixture is sufficient to effectively dissolve the acid salts of long chain amino acid and alkylamine. The extractant solvent is selected on the same principle as described in the previous section for the extractant solvent for the hydrolysis solution with alkali hydroxide.

After dissolution and extraction according to the process of present invention, the aqueous phase containing the acid salts of long chain amino acid and alkylamine and the extractant solvent phase rich in long chain dibasic acid and short chain alkanoic acid are separated. An added advantage of the present invention is that all colored materials are transferred into organic extractant phase and the extracted aqueous solution of long chain amino acid and alkylamine is nearly colorless.

After phase separation, the organic extractant phase is treated in the same way as for the extractant phase obtained from acidification and extraction of the hydrolysis solution using alkali hydroxide.

The strongly acidic aqueous phase is neutralized with a basic agent to a neutral pH in the range of 5 to 9, more preferably 5 to 8, most preferably 6 to 7, to precipitate long chain amino acid. After cooling, the precipitated solid is isolated by means of solid-liquid separation, i.e., filtration or centrifuge.

The basic agent is selected from ammonia, alkali and ammonium salts of hydroxide, bicarbonate, carbonate, bisulfite, sulfite, and carboxylate. Preferably, the basic agent is alkali hydroxide or ammonium hydroxide, and most preferably, sodium hydroxide.

Figure 5:
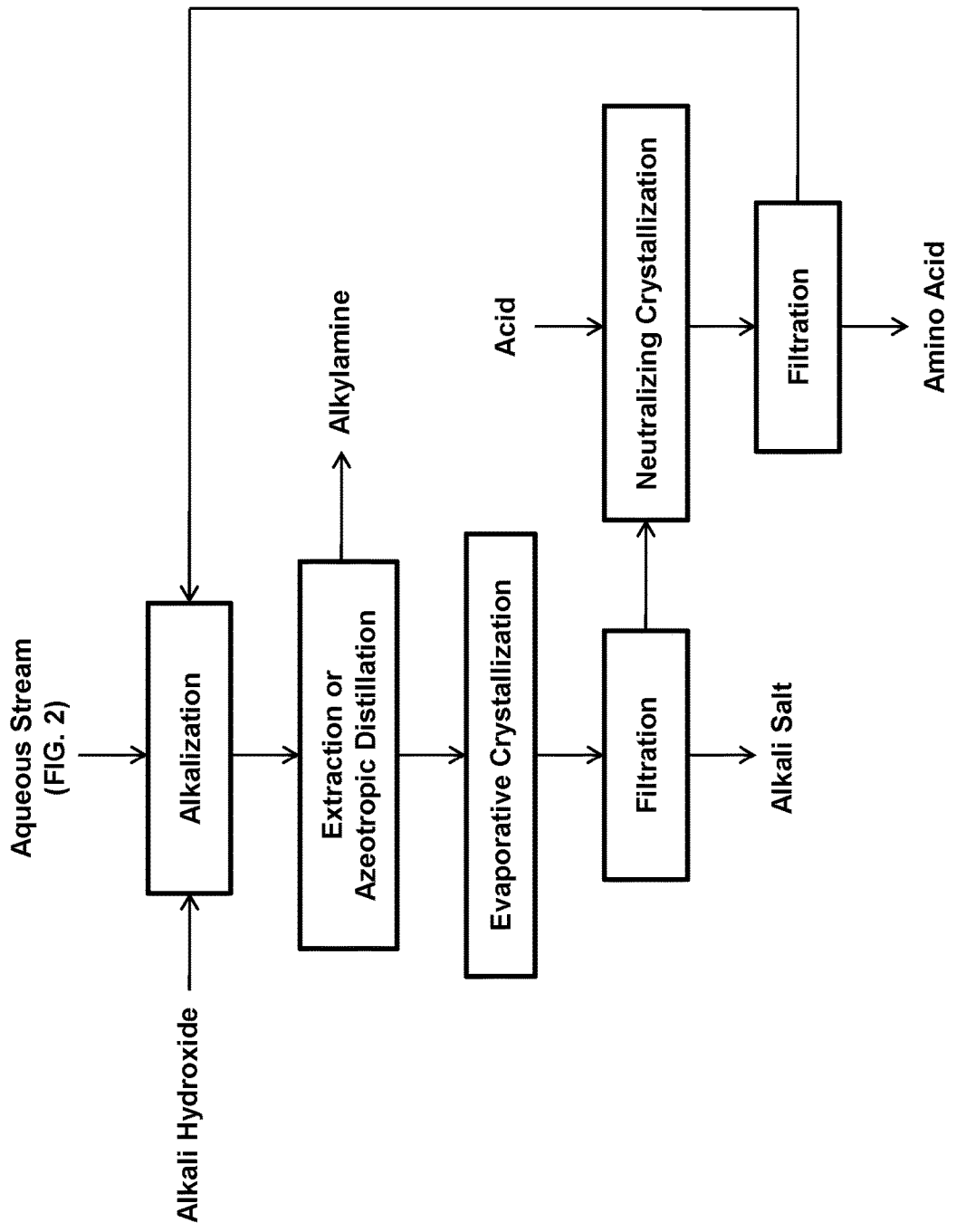
FIG. 5. Schematic flowchart for the treatment of aqueous stream to recover alkylamine, long chain amino acid, and alkali salt for an acid hydrolysis of mixed amide derivatives.

The mother liquor obtained after the isolation of long chain amino acid can be treated according to the scheme illustrated in FIG. 5 to separate alkylamine, inorganic salt, and to recover dissolved long chain amino acid.

When sodium hydroxide is used as the basic agent to neutralize sulfuric acid, more sodium hydroxide is added to the mother liquor to a basic pH, alkylamine can be extracted with an extractant solvent, or preferably by azeotropic distillation. After complete removal of alkylamine, the solution is further evaporated to separate inorganic salt, preferably, sodium sulfate. Long chain amino acids can be recovered by adding an acid to adjust the pH to neutral.

If ammonia or ammonium hydroxide is used as the basic agent to neutralize sulfuric acid, and after more basic agent is added to the mother liquor to a basic pH, alkylamine can only be recovered by extraction. Distillation of the basic solution will remove ammonia instead of alkylamine.

Figure 7:
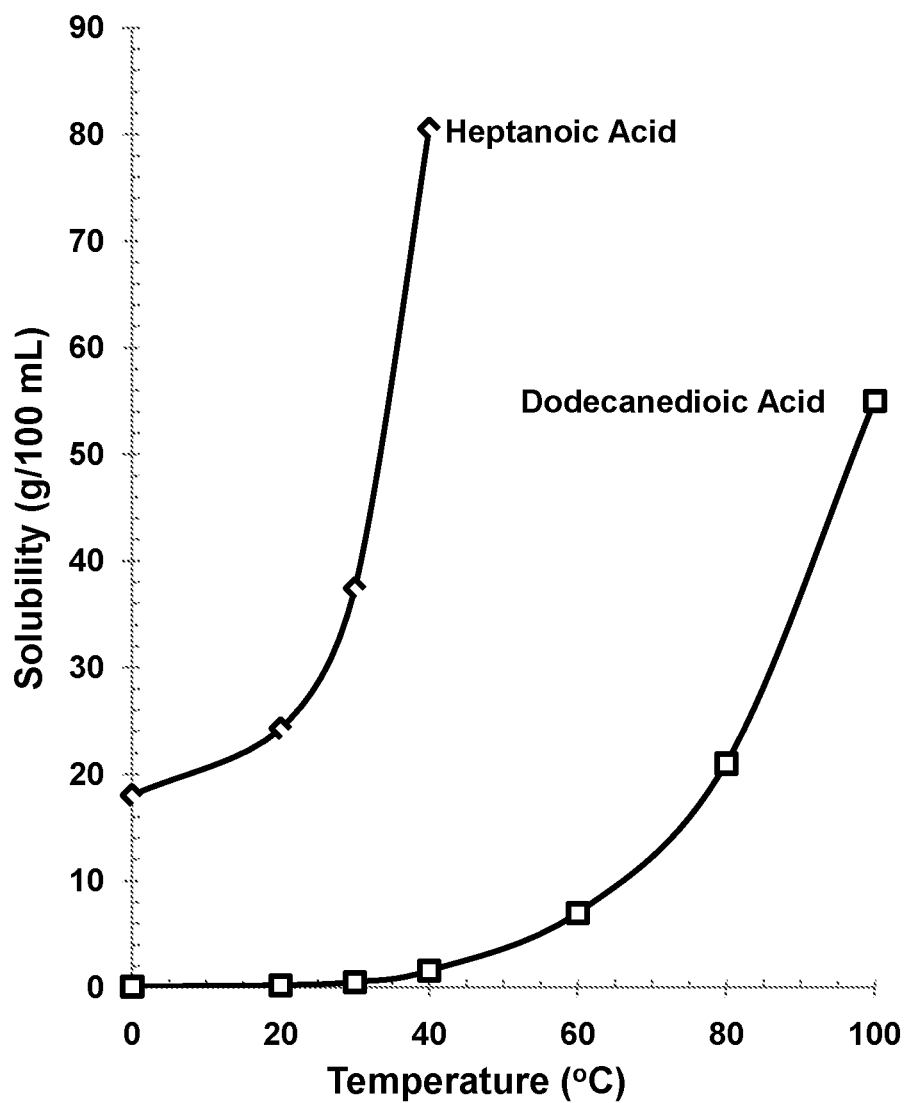
FIG. 7. Solubility curve of heptanoic acid in a 6 M solution of sodium hydroxide and dodecanedioic acid in a 3 M solution of sodium hydroxide.

In an alkali hydroxide hydrolysis of the mixed amide derivatives, two mole equivalents of alkali hydroxide are required, but more than two equivalents, usually between 2.5 to 3 equivalents of alkali hydroxide are used to achieve a complete hydrolysis. The excess basic agent consumes additional acid and generate an extra amount of inorganic salt. The present inventor found that alkali salts of long chain amino acid and dibasic acid have little solubility at room temperature in water or in a solution of alkali hydroxide, as illustrated in FIG. 6 and FIG. 7, and can be crystallized from the hydrolysis solution. Upon cooling, a mixture of alkali salts of long chain dibasic acid and amino acid is precipitated. After separation of these insoluble salts, the excess alkali hydroxide can be recycled to the hydrolysis stage to reduce the use of alkali hydroxide. The recycling can be performed until the concentration of alkali salt of alkanoic acid becomes saturated, at which point, the mother liquor is purged from the hydrolysis stage and acidified with an acid to form alkanoic acid.

Precipitation of the alkali salts of long chain amino acid and dibasic acid can be carried out at temperature from 0° C. to 40° C., preferably from 10° C. to 30° C., most preferably from 15° C. to 25° C. At this preferable temperature, alkali salts are precipitated in high yield.

Alternatively, the hydrolysis solution is cooled to precipitate alkali salts of long chain dibasic acid and amino acid, which are separated by means of a solid-liquid separation to provide a mother liquor. Alkylamine is then recovered from the mother liquor by distillation or extraction with an extractant solvent.

Precipitation of the alkali salts of long chain amino acid and dibasic acid is performed preferably after removal of alkylamine, but the precipitation can also be carried out before removing alkylamine, in fact, little difference is observed if alkylamine is not removed first.

Preferably, alkylamine is removed from the solution before precipitation, because the strongly alkaline hydrolysis solution makes alkylamine removal from the solution convenient to perform by distillation or by extraction with an extractant solvent.

Acidification of the mother liquor with an acid results in the formation of alkanoic acid. The alkanoic acid can be separated by phase separation, or it can be extracted with an extractant solvent. Alkanoic acid of required purity can be obtained by distillation.

The mixed alkali salts of long chain amino acid and dibasic acid can be used directly for the separation or they can first be converted to a mixture of long chain amino acid and dibasic acid before the separation. To prepare a mixture of long chain dibasic acid and amino acid, their alkali salts are dissolved or suspended in water and neutralized with an acid to a pH in the range from 4 to 5. The alkali salts are converted to a mixture of their respective long chain dibasic acid and amino acid.

A mixture of long chain amino acid and dibasic acid can be separated by selectively dissolving long chain dibasic acid in an aqueous solution of ammonia, ammonium hydroxide, ammonium bicarbonate, ammonium carbonate, alkylamines, or a mixture of two or more thereof. Upon removal of excess ammonia or alkylamine by heating, long chain dibasic acid is converted to the ammonium salt, which is soluble in water, while the amino acid is nearly insoluble. The long chain amino acid is recovered by means of solid-liquid filtration, while the long chain dibasic acid, dissolved in the mother liquor as the ammonium salt, is recovered by adding an acid to convert the ammonium salt to long chain dibasic acid.

The mixture of long chain amino acid and dibasic acid or their alkali salts can be separated into long chain amino acid and dibasic acid by first dissolving or suspending in water, adding an acid in the presence of an extractant solvent to form an aqueous solution of an acid salt of long chain amino acid and an extractant solvent phase containing long chain dibasic acid according to process disclosed in the present invention.

Figure 8:
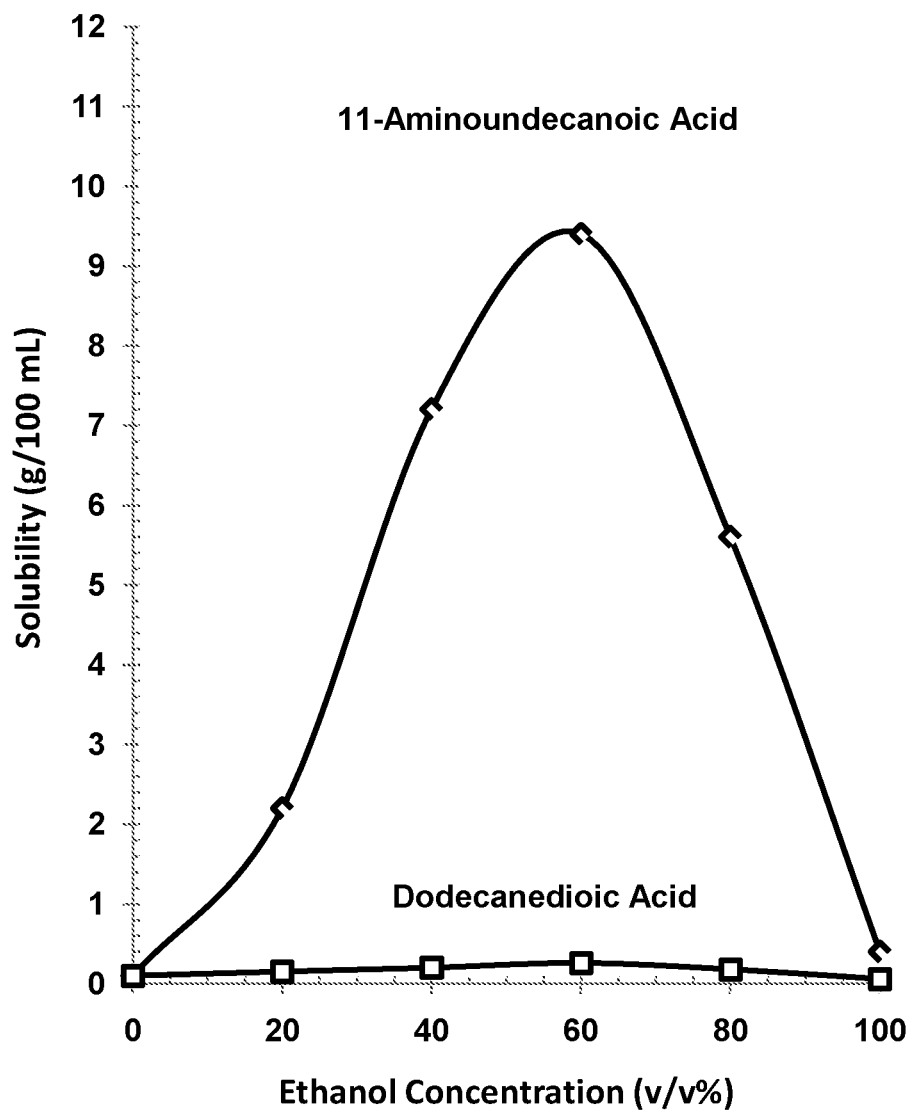
FIG. 8. Solubility of 11-aminoundecanoic acid and dodecanedioic acid in aqueous ethanol solution of 2 M sodium hydroxide at different concentration of ethanol.
Figure 9:
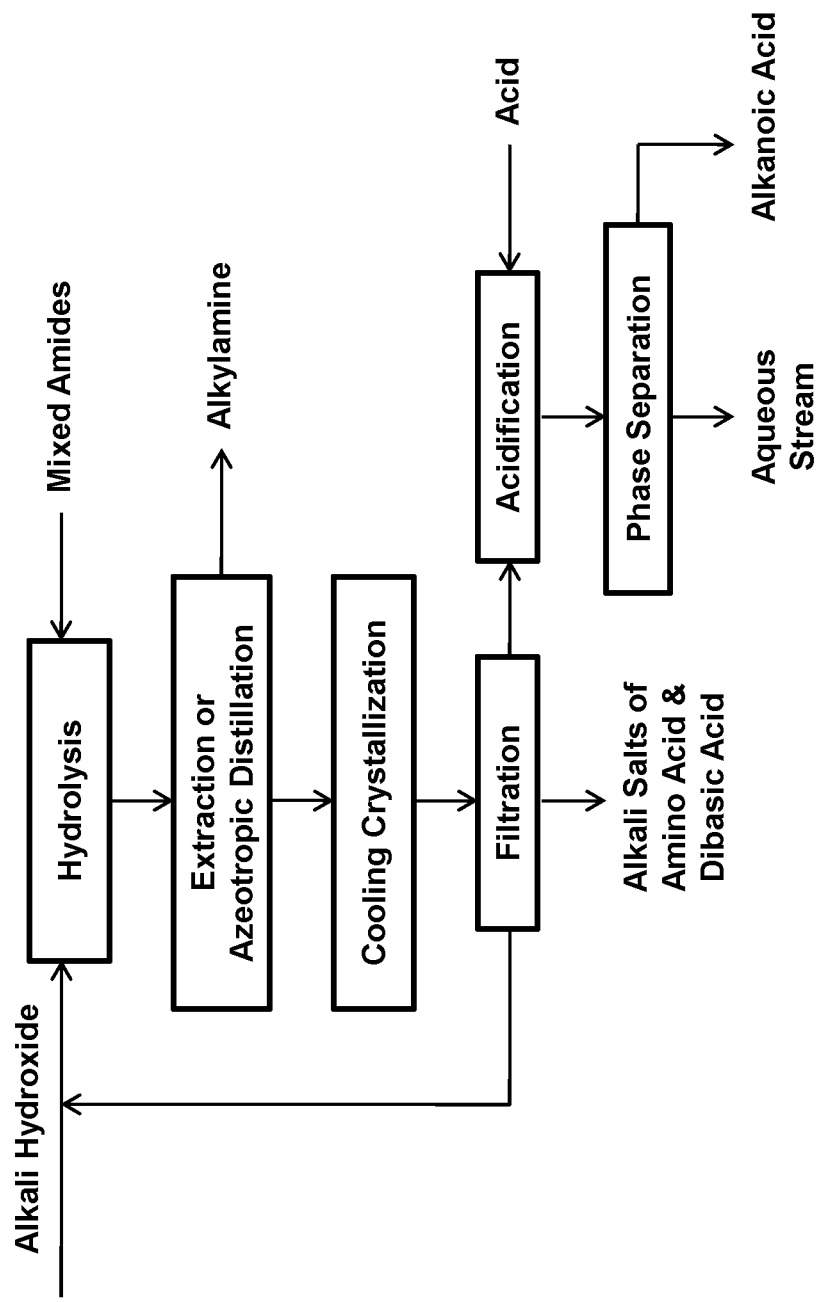
FIG. 9. Schematic flowchart for the separation of alkali salts for long chain amino acid and dibasic acid from a mixture of an alkali hydroxide hydrolysis.
Figure 10:
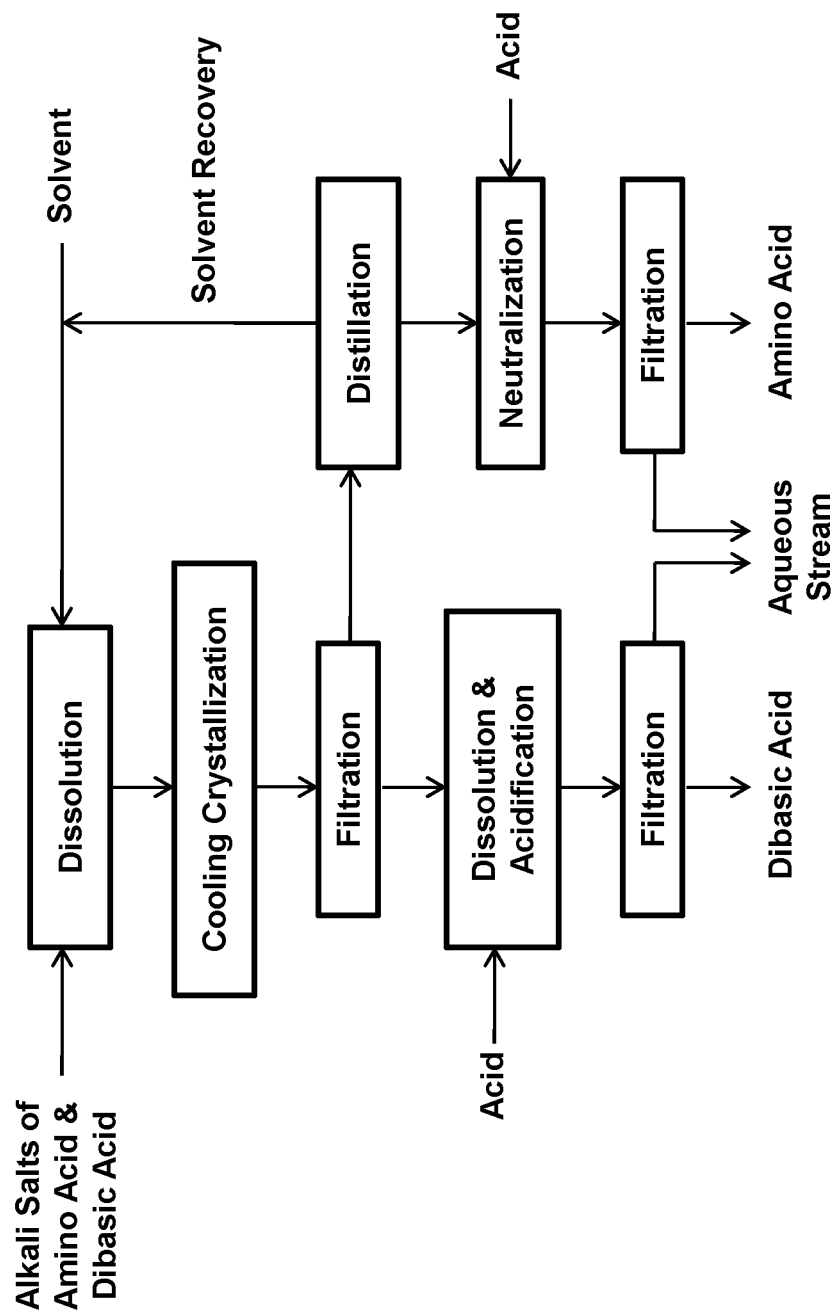
FIG. 10. Schematic flowchart for the separation of alkali salt of long chain amino acid and long chain dibasic acid from their mixture by us of aqueous solvent.

Although the alkali salts are nearly insoluble in water and organic solvents, the present inventor found that the solubility of the alkali salts of long chain amino acid and dibasic acid can be drastically altered by using an aqueous solvent. For example, FIG. 8 illustrates the solubility change of sodium salts of 11-aminoundecanoic acid and dodecanedioic acid in aqueous ethanol. Sodium salts of 11-aminoundecanoic acid and dodecanedioic acid are nearly insoluble in both water and ethanol, but aqueous ethanol drastically increases the solubility of sodium of 11-aminoundecanoic acid, while the sodium salt of dodecanedioic acid remains unchanged. This surprising finding renders the separation of these two salts possible.

Suitable solvents include, but not limited to, methanol, ethanol, propanol, isopropanol, tert-butanol, n-butanol, isobutanol, sec-butanol, ethylene glycol, propylene glycol, diethylene glycol, glycerol, tetrahydrofuran, dioxane, morphine, N-methyl morphine, dimethyl formamide, dimethyl acetamide, N-methylpyrrolidone, tetramethylurea, and a mixture of two or more thereof. Preferable solvent is selected from one of the lower alcohols.

The most preferable solvent is ethanol.

The concentration of aqueous ethanol is from 20% to 90%, preferably from 40% to 80%, most preferably from 50% to 70%.

In order to separate the alkali salts of long chain amino acid and dibasic acid, the mixed salts can be stirred in an aqueous solution of selected solvent at a temperature from 0° C. to 40° C., preferably from 15° C. to 25° C. from 30 minutes to 2 hours. Alkali salt of long chain amino acid dissolves while alkali salt of long chain dibasic acid remains as solid. More preferably, the mixed salts are heated in an aqueous solvent to dissolve, then cooled to crystallize the alkali salt of long chain dibasic acid.

The amount of an aqueous solvent is greater than the effective amount to dissolve alkali salt of long chain amino acid. Too large an amount is to be avoided as a small amount of alkali salt of long chain dibasic acid will dissolve and complicate the separation.

The insoluble alkali salt of long chain dibasic acid in an aqueous solvent is separated by means of solid-liquid separation from soluble alkali salt of long chain amino acid. Long chain dibasic acid is recovered by adding an acid to an aqueous suspension or solution of the alkali salt, then by means of solid-liquid separation.

The mother liquor after the separation of alkali salt of long chain dibasic acid is distilled to recover solvent and the aqueous solution of alkali salt of long chain amino acid is neutralized with an acid to a pH in the range from 5 to 9 to recover the long chain amino acid.

Figure 11:
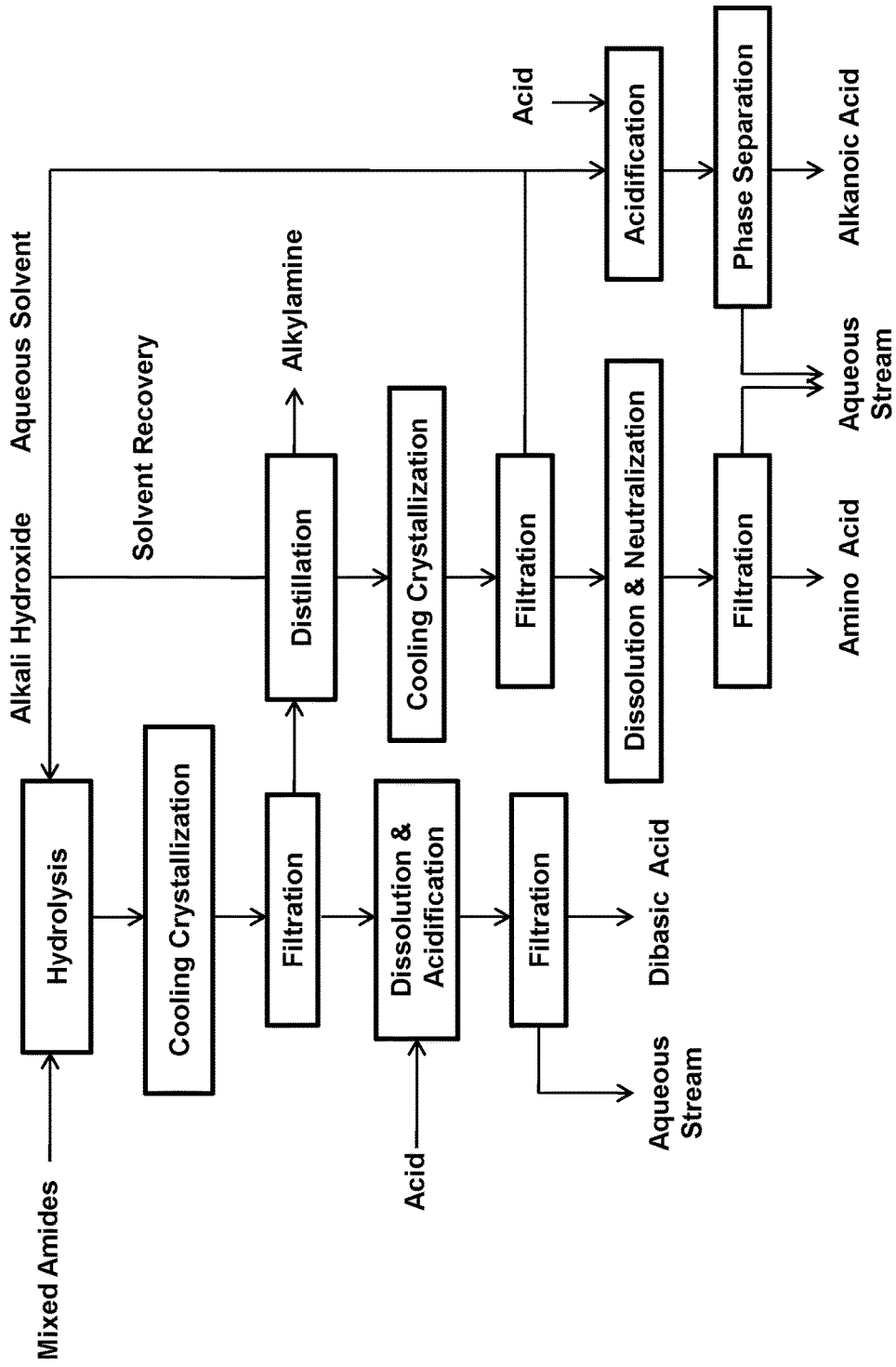
FIG. 11. Schematic flowchart for the separation of long chain amino acid and dibasic acid from a mixture of an alkali hydroxide hydrolysis in an aqueous solvent.

FIG. 11 demonstrates an integrated process for an alkali hydroxide hydrolysis of the mixed amide derivatives in an aqueous solvent, most preferably, ethanol, for a direct isolation of the alkali salt of long chain dibasic acid and the alkali salt of long chain amino acid without isolating their mixture.

After the hydrolysis is completed, the solution is cooled to crystallize the alkali salt of long chain dibasic acid. The crystallization takes place at a temperature in the range from 0° C. to 40° C., more preferably from 15° C. to 25° C. The crystallized salt of long chain dibasic acid is separated by means of solid-liquid separation, i.e., filtration or centrifuge, to provide a mother liquor.

The mother liquor is distilled first to recover solvent and then to remove alkylamine. The residual solution of distillation is then cooled to crystallize the alkali salt of long chain amino acid, which is separated by means of solid-liquid separation, i.e., filtration or centrifuge, to provide a mother liquor containing mainly alkali salt of alkanoic acid. The crystallization of the alkali salt of long chain amino acid takes place at a temperature in the range from 0° C. to 40° C., more preferably from 15° C. to 25° C.

The alkali salt of long chain dibasic acid and amino acid can be further purified by recrystallization in water or an aqueous solvent.

Long chain dibasic acid is obtained by dissolving or suspending the alkali salt in water, acidified to a pH in the range from 1 to 5, more preferably from 3-4, with an acid. After completion of crystallization, the crystalline solid is separated by means of solid-liquid separation.

Long chain amino acid is obtained by dissolving or suspending the alkali salt in water, which is then neutralized with an acid to a pH in the range from 5 to 9, more preferably in the range from 6 to 8.

The mother liquor containing the alkali salt of alkanoic acid also contains excess alkali hydroxide. This solution can be recycled to the hydrolysis stage to make use of the excess alkali hydroxide until the concentration of alkali salt of short chain alkanoic acid becomes saturated. The solution is then purged from the process and acidified with an acid to yield alkanoic acid, which can be isolated by a phase separation or by extraction with an extractant solvent.

Figure 12:
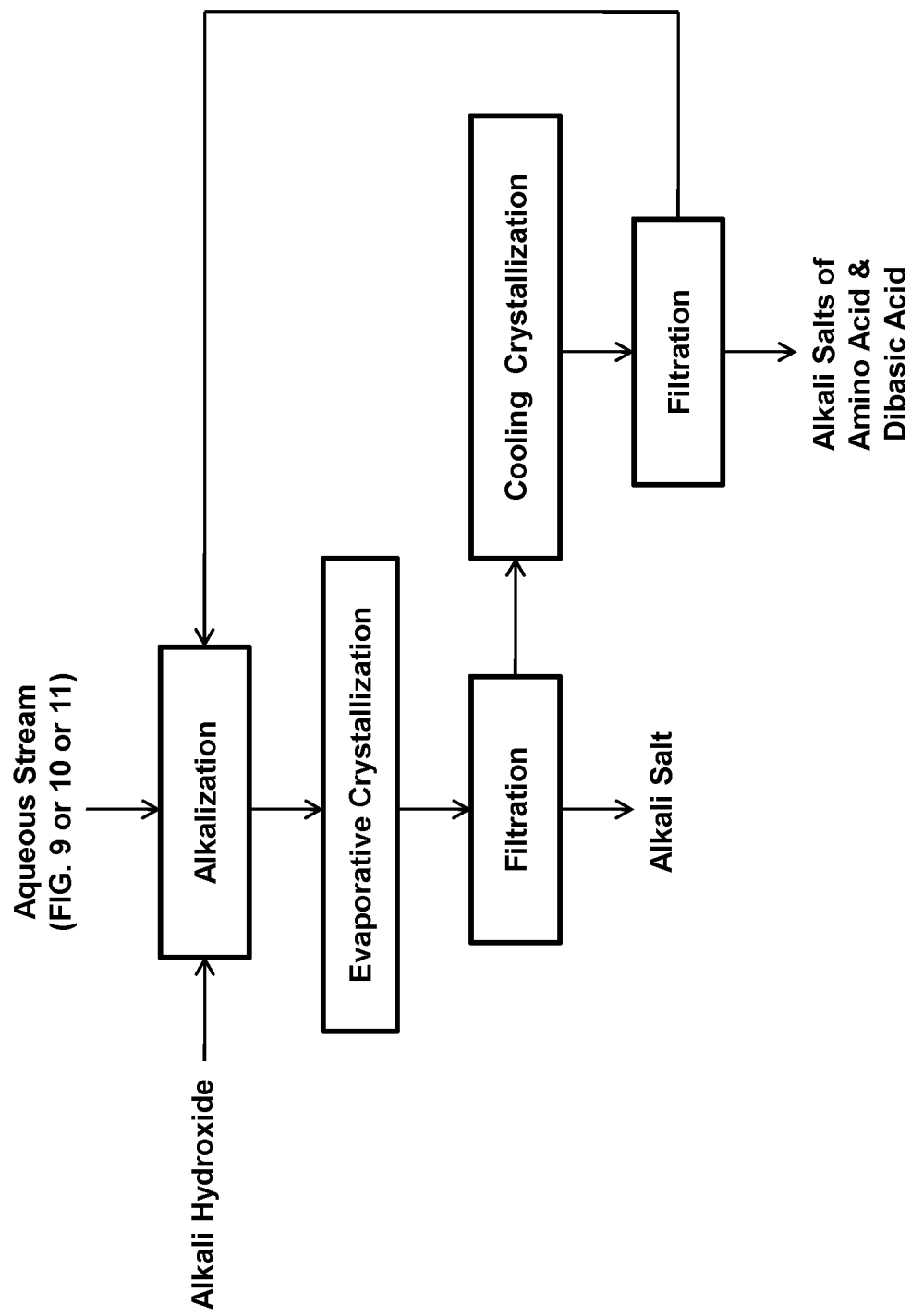
FIG. 12. Schematic flowchart for the separation of inorganic alkali salt and the recovery of the alkali salts of long chain amino acids and dodecanedioic acid from waste aqueous stream.

The aqueous stream, generated as waste water after the separation of long chain amino acid, dibasic acid, or alkanoic acid, contains inorganic salt, most preferably sodium sulfate, if sulfuric acid and sodium hydroxide are selected as the most preferable acid and basic agent respectively, is treated according a scheme illustrated in FIG. 12 to isolate alkali salt and to recover alkali salts of long chain amino acid and dibasic acid. An alkali hydroxide is introduced to an aqueous stream to increase the solubility of alkali salts of long chain amino acid and dibasic acid at higher temperature so as to facilitate the isolation of alkali salt by evaporative crystallization. The mother liquor is then cooled to precipitate a mixture of alkali salts of long chain dibasic acid and amino acid, which is separated by means of solid-liquid separation. The mother liquor is returned to the beginning step to complete a cycle. This cyclic process ensures that no waste, other than inorganic salt, will be discharged from the process.

The process according to the present invention achieves a complete separation of each component in the production of long chain amino acids and dibasic acids without discharging any waste aqueous stream from the process.

EXAMPLES

The following examples illustrate the practice of this invention but are not intended to limit its scope.

Example 1

This example relates to the separation of 11-aminoundecanoic acid, dodecanedioic acid, hexylamine, heptanoic acid, and stearic acid from their mixture obtained from sodium hydroxide hydrolysis of the mixed amide derivatives.

A mixture of the starting solution was obtained by hydrolyzing 150 g of the mixed amide derivatives prepared from methyl 12-ketostearate according to WO2017/088218 with 60 g of sodium hydroxide in 800 mL of water.

The solution was azeotropically distilled with a 2.5×30 cm vacuum jacketed column packed with porcelain berl saddles, first to obtain methanol, then an azeotrope of hexylamine-water until the pH of the overhead became neutral at a pH of 7-8. The distillate was separated into two phases and the lower aqueous phase was continuously returned to the distillation flask. The crude hexylamine was dehydrated by azeotropic distillation to yield 20.5 g of hexylamine.

To the residual solution were added 800 mL of toluene, followed by 100 g of sulfuric acid. The mixture was vigorously stirred for 60 minutes at 85° C. and transferred to a separatory funnel to separate the aqueous phase. The dark-colored upper toluene phase was washed with hot deionized water and the washing was combined with the aqueous phase.

To the colorless aqueous phase was added 1.0 g of activated carbon and stirred at 80° C. for 45 minutes and the solution was filtrated to obtain a clear, colorless solution. The solution was neutralized with a solution of sodium hydroxide to a pH of 7.5 at about 70° C. to yield a crystalline suspension. After cooling to 35° C., the suspension was filtrated and the solid material washed three times with deionized water. After drying, 42.5 g of white 11-aminoundecanoic acid was obtained.

To the mother liquor of about 1200 mL was added 1.0 g of sodium hydroxide. The solution was concentrated and sodium sulfate removed by filtration three times so that 300 mL of solution remained. This basic solution was adjusted with dilute sulfuric acid to a pH of 7.5 to recover another 0.8 g of 11-aminoundecanoic acid.

The toluene solution was washed with hot deionized water once and cooled on ice to 5° C. to obtain a crystalline suspension. After filtration, washing with cold toluene, and drying, 45.2 g of dodecanedioic acid was obtained. The product was off-white.

The toluene filtrate was combined with toluene washing and distilled to recover toluene. The residual was then vacuum distilled with a short path column to yield 24.5 g of heptanoic acid.

The residual after distillation was black and weighted 26.6 g. The residual was mixed with 200 mL of methanol and added 1.0 g of sulfuric acid. After the mixture was refluxed for 2 hours and sulfuric acid was neutralized with sodium methoxide. Methanol was removed by distillation and the residual methyl esters were distilled to obtain a mixture of colorless methyl esters, of which 80% was methyl stearate, 5% was methyl heptanoate, 15% was dimethyl dodecanedioate. About 1.5 g of black residual remained in the distillation flask.

Example 2

This example relates to the separation of 11-aminoundecanoic acid, dodecanedioic Acid, hexylamine, heptanoic acid, and stearic acid from their mixture of sulfuric acid hydrolysis of the mixed amide derivatives.

A mixture of the starting suspension was obtained by hydrolyzing 150 g of the mixed amide derivatives prepared from methyl 12-ketostearate according to WO2017/088218 with a mixture of 150 g of sulfuric acid and 30 g of water. During the hydrolysis, low-boiling methanol was continuously removed.

To the reaction suspension were added 800 g of water and 800 mL of toluene. The mixture was vigorously stirred for 60 minutes at 85° C. and transferred to a separatory funnel to separate the two phases.

The toluene phase was treated the same way as in Example 1 and similar results were obtained for each component.

The aqueous phase was neutralized with aqueous solution of sodium hydroxide to neutral pH at 7.5 for a total of 115 g of sodium hydroxide. After cooling to 35° C., the crystalline solid was filtered off, washed three times with deionized water, dried to yield 41.6 g of 11-aminoundecanoic acid.

To the mother liquor was added an additional solution of sodium hydroxide containing 20 g of sodium hydroxide. The solution was azeotropically distilled with a 2.5×30 cm vacuum jacketed column filled with porcelain berl saddles until the pH of the overhead became a pH of 7-8. The distillate is separated into two phases and the lower aqueous phase was continuously returned to the distillation flask. The crude hexylamine was dehydrated by azeotropic distillation to yield 21.5 g of hexylamine.

After hexylamine was completely removed, the solution containing sodium sulfate was treated the same way as in Example 1. An additional 1.2 g of 11-aminoundecanoic acid was recovered from the mother liquor.

Example 3

This example relates to the separation of 9-aminononanoic acid, sebacic acid, octylamine, and pelargonic acid.

A mixture of the starting solution was obtained by hydrolyzing 150 g of the mixed amide derivatives prepared from methyl 10-ketostearate according to WO2017/088218 with 60 g of sodium hydroxide in 800 mL of water.

To the turbid solution was added 200 mL of toluene and the mixture was vigorously stirred at a temperature of 80° C. for 45 minutes. Afterwards, the toluene phase was separated and removed to yield a residual, which was distilled to obtain 29.5 g of n-octylamine.

The aqueous phase was treated the same way as in Example 1 to obtain 36.9 g of pelargonic acid, 39.6 g of 9-aminononanoic acid, and 45.5 g of sebacic acid.

Example 4

This example relates to the separation of 13-aminotridecanoic acid, brassylic acid, hexylamine, and heptanoic acid.

A mixture of the starting solution was obtained by hydrolyzing 180 g of the mixed amide derivatives prepared from methyl ester of 14-ketoarachidic acid according to WO2017/088218 with 60 g of sodium hydroxide in 800 mL of water.

The reaction solution was treated the same way as in Example 1 to yield 23.5 g of hexylamine, 29.4 g of heptanoic acid, 53.1 g of 13-aminotridecanoic acid, and 62.9 g of brassylic acid.

Example 5

This example relates to the separation of 11-aminoundecanoic acid, dodecanedioic acid, hexylamine, heptanoic acid, and stearic acid by the method of co-precipitation of sodium salts of 11-aminoundecanoic acid and dodecanedioic acid.

A mixture of the starting solution was obtained by hydrolyzing 150 g of the mixed amide derivatives prepared from methyl 12-ketostearate according to WO2017/088218 with 60 g of sodium hydroxide in 800 mL of water.

The solution was azeotropically distilled with a 2.5×30 cm vacuum jacketed column packed with porcelain berl saddles, first to obtain methanol, then an azeotrope of hexylamine-water until the pH of the overhead became neutral at a pH of 7-8. The distillate was separated into two phases and the lower aqueous phase was continuously returned to the distillation flask. The crude hexylamine was dehydrated by azeotropic distillation to yield 20.5 g of hexylamine.

To the residual solution of distillation was added 500 mL of water. The solution was slowly stirred while cooling to room temperature. The precipitate was then filtered and washed with cold water to give a mixture of the alkali salts of 11-aminoundecanoic acid and dodecanedioic acid. Half of the mother liquor is recycled to the hydrolysis stage. The other half is concentrated to 300 mL and acidified with sulfuric acid to yield an oily layer of heptanoic acid.

The solid material was dissolved in 500 mL of 65% aqueous ethanol by heating and then slowed cooled to room temperature to crystallize sodium salt of dodecanedioic acid. After filtration and washing with water, the mother liquor is distilled to recover ethanol and the aqueous solution was neutralized with sulfuric acid to a pH of 6-7 to yield 41.4 g of 11-aminoundecanoic acid.

The sodium salt of dodecanedioic acid was suspended in 400 mL of water and acidified with sulfuric acid to yield 46.3 g of dodecanedioic acid.

Example 6

This example relates to the sodium hydroxide hydrolysis of the mixed amide derivatives in aqueous ethanol and the separation of 11-aminoundecanoic acid, dodecanedioic acid, hexylamine, and heptanoic acid.

A mixture of the starting solution was obtained by hydrolyzing 160 g of the mixed amide ethyl ester prepared from ethyl 10-ketostearate according to WO2017/088218 with 60 g of sodium hydroxide in 800 mL of 65% aqueous ethanol.

The solution after hydrolysis was cooled slowly to room temperature and the crystallized sodium salt of dodecanedioic acid was filtered and washed with dilute aqueous ethanol. The solid material was suspended in 300 mL of water, to which was added sufficient sulfuric acid to a pH of 2. The solid material was filtered and washed three times with deionized water to give 46.8 g of dodecanedioic acid.

The alcoholic mother liquor was distilled with a 2.5×30 cm vacuum jacketed column packed with porcelain berl saddles, first to obtain ethanol, then an azeotrope of hexylamine-water until the pH of the overhead became neutral at a pH of 7-8. The distillate was separated into two phases and the lower aqueous phase was continuously returned to the distillation flask. The crude hexylamine was dehydrated by azeotropic distillation to yield 21.4 g of hexylamine.

To the residual solution of ethanol distillation was added 400 mL of water. The solution was slowly stirred while being cooled to room temperature to crystallize sodium salt of 11-aminoundecanoic acid. After filtration and washing with water, the solid was suspended in 200 mL of water and neutralized with sulfuric acid to a pH of 7.5. Filtration, washing with deionized water, and drying, yield 40.9 g of 11-aminoundecanoic acid.

The mother liquor after separating the sodium salt of 11-aminoundecanoic acid was concentrated to a volume of 300 mL, and acidified with sulfuric acid to give an oily upper layer of heptanoic acid, which was separated by phase separation.

The aqueous streams were combined and added 2 g of sodium hydroxide. The solution were boiling to crystallize sodium sulfate, which was filtered at 80° C. and washed with hot saturated solution of sodium sulfate. The mother is then cooled slowly to 35° C. to crystallize sodium salt of 11-aminoundecanoic acid and dodecanedioic acid, which was recovered by filtration.

It will be understood that the foregoing examples, explanation, and drawings are for illustrative purpose only and that in view of the instant disclosure various modifications of the present invention will be self-evident to those skilled in the art and are to be included within the spirit and purview of this application and the scope of the claims.

What is claimed is:

1. A process for the separation from an aqueous stream of long chain amino acid, dibasic acid, short chain alkylamine, and alkanoic acid of the following structures:

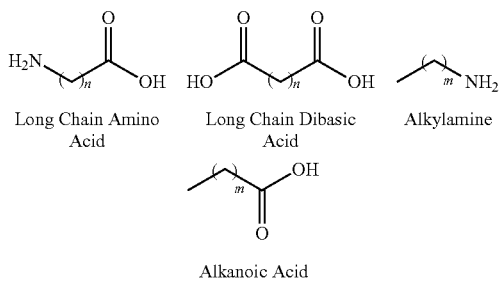

from at least two of them in an alkali hydroxide hydrolysis mixture of the mixed amide derivatives of the following structures:

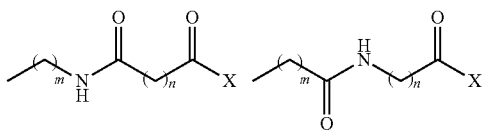

wherein m is an integer from 0 to 10;
n is an integer from 6 to 20;
X is OR or $NR_1R_2$, wherein OR is OH, $C_1$-$C_8$ monohydric alcohol, or $C_1$-$C_8$ polyhydric alcohol, and $R_1$ and $R_2$ are each independently hydrogen or $C_1$-$C_8$ alkyl group;
comprising:
(1) cooling the alkali hydroxide hydrolysis solution of mixed amides to precipitate a mixture of alkali salts of long chain amino acid and dibasic acid;
(2) separating the mixture of alkali salts of long chain amino acid and dibasic acid by means of solid-liquid separation to provide a mother liquor comprising alkali salt of alkanoic acid; and
(3) separating long chain amino acid and dibasic acid from their mixture or a mixture of their alkali salts by acidification-extraction of long chain dibasic acid with an extractant solvent and an acid, or by selective dissolution of the alkali salt of long chain amino acid in an aqueous solvent, or by selective dissolution of long chain dibasic acid in an aqueous solution of ammonium hydroxide, or ammonium bicarbonate, or ammonium carbonate or their mixture.

2. The process according to claim 1, wherein mixed alkali salts of long chain amino acid and dibasic acid are precipitated at a temperature from 0° C. to 40° C.

3. The process according to claim 1, wherein mixed alkali salts of long chain amino acid and dibasic acid are precipitated at a temperature from 15° C. to 25° C.

4. The process according to claim 1, wherein an aqueous solvent for separating alkali salts of long chain amino acid and dibasic acid is selected from the group consisting of an aqueous solution of methanol, ethanol, propanol, isopropanol, tert-butanol, n-butanol, isobutanol, sec-butanol, ethylene glycol, propylene glycol, diethylene glycol, glycerol, tetrahydrofuran, dioxane, morphine, N-methylmorphine, dimethylformamide, dimethyl acetamide, N-methylpyrrolidone, tetramethylurea, and a mixture of two or more thereof.

5. The process according to claim 1, wherein the aqueous solvent is aqueous ethanol.

6. The process according to claim 5, wherein the aqueous ethanol contains from 20% to 90% of ethanol.

7. The process according to claim 5, wherein the aqueous ethanol contains from 40% to 70% of ethanol.

8. The process according to claim 1, wherein a process for preparing a mixture of long chain dibasic acid and amino acid from their alkali salts in step (3) comprises:
(a) adding an acid to an aqueous solution or suspension of the alkali salts of long chain dibasic acid and amino acid to a pH in the range from 4 to 5; and
(b) separating the mixture of long chain dibasic acid and amino acid by means of solid-liquid separation.

9. The process according to claim 1, wherein a process for separating long chain amino acid and dibasic acid from their mixture in step (3) comprises:
(a) suspending the mixture of long chain amino and dibasic acid in an aqueous solution of ammonia or ammonium hydroxide, or ammonium bicarbonate, or ammonium carbonate, or their mixture to dissolve long chain dibasic acid;
(b) separating long chain amino acid by means of solid-liquid separation to provide a mother liquor; and
(c) adding an acid to the mother liquor of step (b) to precipitate long chain dibasic acid.

10. The process according to claim 1, wherein a process for separating long chain amino acid and dibasic acid in step (3) comprises:
(a) adding an acid to an aqueous suspension or solution of a mixture of long chain amino acid and dibasic acid or a mixture of the alkali salts of long chain amino acid and dibasic acid in the presence of an extractant solvent;
(b) separating the mixture of step (a) into an aqueous phase containing the acid salt of long chain amino acid and an extractant phase containing long chain dibasic acid;
(c) neutralizing the aqueous phase of step (b) with a basic agent to yield long chain amino acid;
(d) cooling the extractant phase to crystallize the long chain dibasic acid; and
(e) separating the long chain dibasic acid by means of solid-liquid separation.

11. The process according to claim 1, wherein a process for separating long chain amino acid and dibasic acid in step (3) comprises:
(a) suspending or dissolving mixed alkali salts of long chain amino acid and dibasic acid in an aqueous solvent;

(b) cooling to crystallize the alkali salt of long chain dibasic acid;
(c) separating the precipitate by means of solid-liquid separation to provide a mother liquor;
(d) adding an acid to an aqueous suspension or solution of the precipitate of step (c) to acidic pH to yield long chain dibasic acid; and
(e) distilling the mother liquor of step (c) to recover solvent and adding an acid to neutralize the solution to yield long chain amino acid.

12. The process according to claim 1, wherein a process for treating the aqueous stream to recover inorganic alkali salt and a mixture of alkali salts of long chain dibasic acid and amino acid comprises:
(a) adding an alkali hydroxide to the aqueous stream to increase the solubility of long chain dibasic acid and amino acid;
(b) concentrating the solution of step (a) to crystallize the inorganic alkali salt and to remove the solid by liquid-solid separation to provide a mother liquor;
(c) cooling the mother liquor of step (b) to precipitate a mixture of alkali salts of long chain dibasic acid and amino acid; and
(d) separating the mixture of alkali salts of long chain dibasic acid and amino acid by solid-liquid separation.

13. The process according to claim 1, wherein the acid is selected from the group consisting of hydrochloric acid, hydrobromic acid, hydroiodic acid, sulfuric acid, nitric acid, phosphoric acid, methanesulfonic acid, ethanesulfonic acid, propanesulfonic acid, isethionic acid, benzenesulfonic acid, toluenesulfonic acid, xylenesulfonic acid, sulfamic acid, malic acid, maleic acid, tartaric acid, glycolic acid, lactic acid, citric acid, oxalic acid, formic acid, acetic acid, propionic acid, and a mixture of two or more thereof.

14. The process according to claim 1, wherein the extractant solvent is selected from the group consisting of butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone, and a mixture of two or more thereof.

15. The process according to claim 1, wherein the long chain amino acids are 9-aminononanoic acid, 11-aminoundecanoic acid, or 13-aminotridecanoic acid.

16. The process according to claim 1, wherein the long chain amino acid is 11-aminoundecanoic acid.

17. The process according to claim 1, wherein the long chain dibasic acids are sebacic acid, dodecanedioic acid, or brassylic acid.

18. The process according to claim 1, wherein the long chain dibasic acid is dodecanedioic acid.

19. The process according to claim 1, wherein the short chain alkanoic acid is heptanoic acid.

20. The process according to claim 1, wherein the alkylamine is n-hexylamine.

21. The process according to claim 1, wherein alkali hydroxides are lithium, sodium, potassium or cesium hydroxide.

22. The process according to claim 1, wherein alkylamine is recovered from the alkali hydrolysis solution of mixed amides by distillation or by extraction with an extractant solvent.

23. The process according to claim 22, wherein the extractant solvent is selected from the group consisting of butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone, and a mixture of two or more thereof.

24. The process according to claim 1, wherein the mother liquor comprising the alkali salt of alkanoic acid is acidified with an acid to yield alkanoic acid.

25. The process according to claim 24, wherein the acid is selected from the group consisting of hydrochloric acid, hydrobromic acid, hydroiodic acid, sulfuric acid, nitric acid, phosphoric acid, methanesulfonic acid, ethanesulfonic acid, propanesulfonic acid, isethionic acid, benzenesulfonic acid, toluenesulfonic acid, xylenesulfonic acid, sulfamic acid, malic acid, maleic acid, tartaric acid, glycolic acid, lactic acid, citric acid, oxalic acid, formic acid, acetic acid, propionic acid, and a mixture of two or more thereof.

* * * * *